United States Patent [19]
Monsivais

[11] Patent Number: 5,458,118
[45] Date of Patent: Oct. 17, 1995

[54] QUANTITATIVE NEURAL PERCUSSION HAMMER

[76] Inventor: Jose J. Monsivais, 716 Twin Hills, El Paso, Tex. 79912

[21] Appl. No.: 237,040

[22] Filed: May 3, 1994

[51] Int. Cl.⁶ .................................................. A61B 10/00
[52] U.S. Cl. ....................................... 128/740; 128/744
[58] Field of Search ................................. 128/630, 740, 128/774, 782, 779

[56] References Cited

U.S. PATENT DOCUMENTS

| | | |
|---|---|---|
| 2,685,286 | 8/1954 | Torricelli ................................. 128/2 |
| 2,716,978 | 9/1955 | Torricelli ............................... 128/740 |
| 2,744,520 | 5/1956 | Torricelli ................................. 128/2 |
| 2,800,895 | 7/1957 | Torricelli . |
| 3,626,927 | 12/1971 | Breneman ............................. 128/740 |
| 4,235,293 | 11/1980 | Saha ..................................... 128/740 |
| 4,505,278 | 3/1985 | Alban ................................... 128/774 |
| 4,643,195 | 2/1987 | Friedman ............................. 128/740 |
| 4,964,412 | 10/1990 | Kelly ................................... 128/740 |
| 5,195,532 | 3/1993 | Schumacher et al. ................ 128/739 |
| 5,301,683 | 4/1994 | Durkan ............................ 128/774 X |

Primary Examiner—Sam Rimell
Attorney, Agent, or Firm—John J. Byrne

[57] ABSTRACT

A diagnostic device and method for determining the presence of a Tinel sign in a patient by providing a calibrated striking unit for use at a selected point along a regenerating nerve and said results of the striking being analyzed with respect to that of a healthy nerve.

5 Claims, 2 Drawing Sheets

QUANTITATIVE NEURAL PERCUSSION HAMMER

BACKGROUND OF THE INVENTION

Tinel's Sign: (Named after French neurosurgeon Jules Tinels, 1879–1952). Tinel's sign is a tingling sensation in the distal part of an extremity in response to pressure or percussion over the site of a partially divided nerve. It can signify regeneration of the nerve.

Evaluation of the state of regeneration of peripheral nerves oftentimes involve attempts to elicit a Tinel's sign. Unfortunately, clinicians try and elicit this sign using varying degrees of force when percussing the nerve. However, any nerve will "tingle" if hit with enough force; hitting one's "funny bone" is an example. Such tingling is a positive percussion result rather than a sign of a regenerating nerve. Therefore, there can be a high incidence of false positive Tinel's signs due to high degrees of percussion force as well as a missed Tinel's sign because of too little force.

During World War I, two different physicians observed, independently of each other, that when a damaged sensory nerve is regenerating the patient experiences a tingling sensation in the area of skin supplied by that nerve. As the nerve regenerates, the sensation moves distally on the extremity, and the sign can be produced by tapping the course of the nerve on the wounded extremity. Hoffman in Germany and Jules Tinel in France both reported this phenomena in 1915, and although Hoffman actually published first, it was Tinel who received credit. In his later works, Tinel noted that the tingling sensation appeared 4–6 weeks after injury and he hypothesized that it was caused by regenerating axons.

Since that time, the inferences that can be determined from a Tinel's sign has diverged markedly from its original conception. A literature review discloses that there is really no consensus on what it actually indicates. In 1966, Phalen[1] tested 654 hands with carpal tunnel syndrome and found the Tinel's sign was present in 73% of them. He concluded it was a good diagnostic sign of an entrapped nerve. However, Stewart and Eisen[2] in 1978 determined that Tinel's sign had little diagnostic value. In a series of patients with carpal tunnel syndrome, 45% had a positive percussion test and, in a series of patients without carpal tunnel syndrome, 29% had a positive reading. They concluded that Tinel's sign was of little diagnostic value. Reports by Heller[3] in 1986, Seror[4] in 1987, and Katz[5] in 1990 also concluded the Tinel sign had little diagnostic value.

[1]Phalen, G. S. The carpal tunnel syndrome. Seventeen year's experience in diagnosis and treatment of six hundred fifty-four hands. *The Journal of Bone and Joint Surgery*, 48-A (2): 211–228, 1966.
[2]Tinels sign and the carpal tunnel syndrome. *British Medical Journal*, 1125–1126, Oct. 21, 1978.
[3]Heller, L., Ring, H., Costeff, H., and Solzi, P. Evaluation of Tinel's and Phalen's signs in the diagnosis of the carpal tunnel syndrome. *Eur. Neuro*, 25:40–42, 1986.
[4]Seror, P. Tinel's sign in the diagnosis of carpal tunnel syndrome. *The Journal of Hand Surgery*, 12-B (3):364–365, 1987.
[5]Katz, J. N., Larson, M. G., Sabra, A. Krarup, C., Stirrat, C. R., Sethi, R., Eaton, H. M., Fossel, A. H., & Liang, M. H. The carpal tunnel syndrome: Diagnostic utility of the history and physical examination findings. *Annals of Internal Medicine*, 112:321–327, 1990.

More recently, applicant conducted tests to determine at what threshold force a positive percussion test is elicited for each of seven nerve locations in the forearm. With knowledge of the amount of force necessary to produce a positive test in healthy subjects, examiners could use a lesser force to ensure that the response was a true Tinel's sign and not simply the nerve responding to an excessive amount of force.

Testing was done using specially designed hammers capable of delivering a precise force of 1, 2, 3, 4, or 5 pounds. Seven locations on each forearm were tested a multiple of times at each level using each weight force on each location. If a subject felt tingling and paresthesia following an impact it was counted as a positive response. This is termed the threshold force; e.g. the lowest force which elicited the tingling sensation for each location.

The seven specific locations tested were: (1) The radial nerve in the forearm under cover of the brachioradialis muscle near the lateral epicondyle of the humerus; (2) The median nerve where it passes between the two heads of the pronator teres in the antecubital fossa; (3) The median nerve where it lies deep to the flexor carpi radialis at the wrist; (4) The ulnar nerve where it passes behind the medial epicondyle at the elbow; (5) The ulnar nerve under cover of the flexor carpi ulnaris and under the flexor retinaculum at wrist; (6) The ulnar nerve at the carpus next to the pisiform bone, and (7) The median nerve at the base of thenar eminence. These seven locations include all the nerves in the forearms which are accessible to surface touch.

Threshold readings were as follows: Site number 1, the radial nerve in the forearm near the epicondyle of the humerus—3 pounds (5.8% false positive rate); Site number 2, the median nerve in the antecubital fossa—4 pounds (4.2% false positive rate); Site number 3, the median nerve at the wrist—3 pounds (10% false positive rate); Site number 4, the ulnar nerve at the elbow—2 pounds (10.8% false positive rate); Site number 5, the ulnar nerve at the wrist—3 pounds (5% false positive rate); Site number 6, the ulnar nerve at the carpus next to the pisiform bone at the base of the palm—2 pounds (5% false positive rate); and Site number 7, the median nerve at the base of the thenar eminence—3 pounds (5% false positive rate).

The results showed the ulnar nerve at the elbow had the lowest threshold for a positive response; that is, it took less force to elicit a positive percussion test in this location than the other locations. It took only two pounds of force to elicit a tingling response in 10% of the subjects. At the other end of the spectrum, the median nerve at the antecubital fossa had the highest threshold for a positive response, that is, it took more force to elicit a positive percussion test in this location than the other locations. It took four pounds of force to elicit tingling sensation in only 4.2% of the subjects, and even at five pounds, only 6.7% had a positive response.

It was determined that each nerve has a specific threshold force which will elicit a positive percussion test. Laplace's law states that Tension=Transmural Pressure×Radius of the Cylinder. In other words, percussing with great force over the nerve will increase the pressure inside the nerve to the point where the nerve will depolarize and give a tingling sensation. If the nerve is percussed at this force or above, the positive reaction may be falsely interpreted as a Tinel's sign.

The differing force necessary at each location can be explained by how close to the surface the nerve is. Nerves which lie just under the skin require less force to elicit a response than those which lie under tendon and muscle. In addition, nerves which are already under pressure from disease or injury will depolarize more rapidly than a nerve not under pressure. Injured nerves, therefore, require less force to elicit a response.

With reference to the prior art, Alban, 4,505,278 discloses a plunger-type device to measure pain thresholds. It is a gradual pressure device that would not work in applicant's methods. The Torricelli patents, 2,685,286; 2,744,520 and 2,800,895, disclose spring charged reflex guns for striking reflex nerve areas. There are no standards with which the force has been calculated. The Torricelli design are apparently to act as a replacement for the ordinary reflex hammer found in most medical offices. In each device, Torricelli obtains his strength by degree of compression. Applicant, on the other hand, first determines the force necessary and then uses a force to accurately administer that force. The spring is biased the same amount for each strike.

SUMMARY OF THE INVENTION

It is a primary objective of this invention to create a method and structure for administering percussion strokes to a patient with a selected force that will diminish the likelihood of false Tinel readings.

Another important objective of this invention is to provide a transportable and adjustable device that can locate a force-producing hammer for various selected nerves of the body so that an accurate percussion force is administered.

Another important objective of this invention is to provide a device which readily accepts springs of various force levels so that a hammer can accurately strike nerve locations selected by a user.

Another objective of the invention is to provide an inexpensive device that can be used to utilize the methods of this invention with a considerable degree of accuracy.

Further advantages and objectives of the invention will be better understood after viewing the drawings and reading of the following description of a preferred embodiment.

DESCRIPTION OF THE PREFERRED EMBODIMENT

Figure 1:
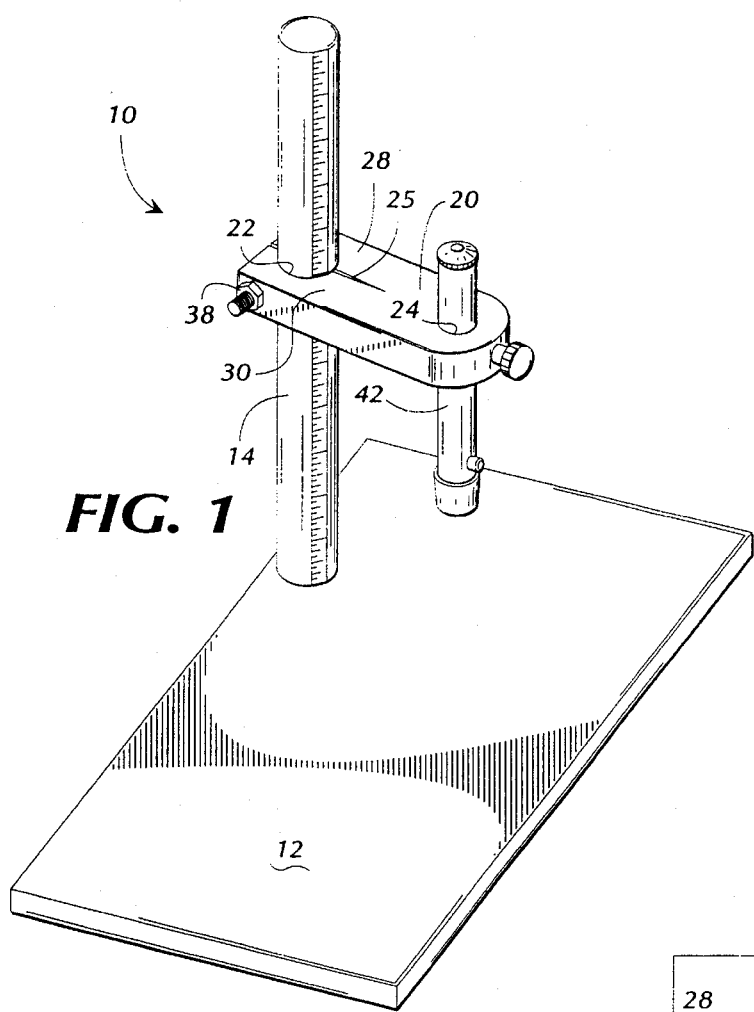
FIG. 1 is a perspective of the device of this invention.

Turning now to the drawings wherein like numerals indicate like parts, the numeral 10 indicates the device of this invention. The device includes a generally rectangular base member 12 upon which a patient's arm or hand can rest.

A vertical standard 14 is secured at its lower end to the base 12 and is perpendicular thereto. Any conventional securing means can be used. The standard has indicia throughout its length and such indicia is indicated by the numeral 16.

A bracket 20 is slidably received along the length of standard 14. The bracket 20 is generally planar and has a pair of openings 22 and 24 at either end thereof. The opening 22 is sized to closely approximate the cross-sectional dimension of standard 14. The bracket is partially divided by longitudinal split 25. The vertical plane of the split 25 traverses the opening 22 and the resulting arms 28 and 30 provide a chuck or vise to receive standard 14. When the standard 14 is slipped into opening 22, the arms 28 and 30 of the chuck lie on either side thereof. Coaxial openings 32 and 34 are formed transversely through the arms to receive the threaded screw 36. The end portion of screw 36 threadably engages nut 38 so that the bracket can be securely fastened to standard 14 at a selected point along its length. The screw member is bent at its outer end to form an operating handle 40.

At its other end, the bracket is formed with the second opening 24 to receive a percussion hammer or tappet 42. As seen best in FIG. 4, the tappet 42 is comprised of a cylinder member 44 having a threaded enclosing cap 46 at the upper end thereof. The other end of cylinder 44 is formed with an opening 48 to receive the shaft 50 of a piston 52. At its outer (lower) end, the piston 52 is equipped with a percussion head or dome 54. The dome can be lightly padded for comfort. At its other end, the shaft 50 is equipped with an enlarged head 56 which engages a coil spring 60. The coil spring 60 is housed in the cylindrical chamber 62 formed between the head 56, the cap 46 and the wall of cylinder 44.

The lower end of cylinder 44 is formed with a radially disposed opening 66 to receive a latch 68 slidably therein. The opening 66 is formed with an enlarged chamber 70 to receive a coil spring 72. The latch 68 is formed with an annular ridge 74 so that the latch 68 is biased inwardly by spring 72.

Figure 4:
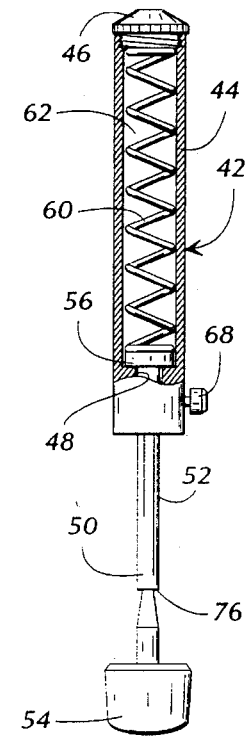
FIG. 4 is a partial cross section of the percussion instrument of this invention.
Figure 2:
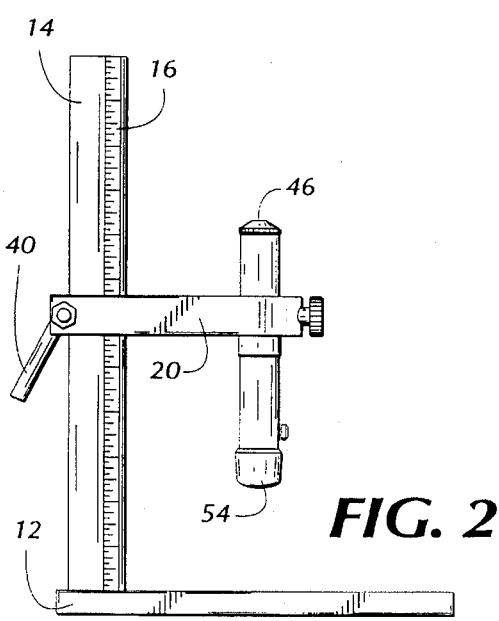
FIG. 2 is a side elevation of the device of FIG. 1.
Figure 3:
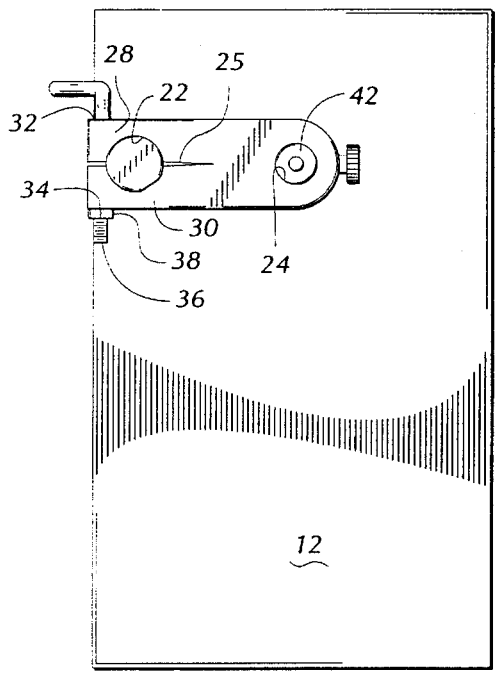
FIG. 3 is a top plan of the device of FIG. 1.
Figure 7:
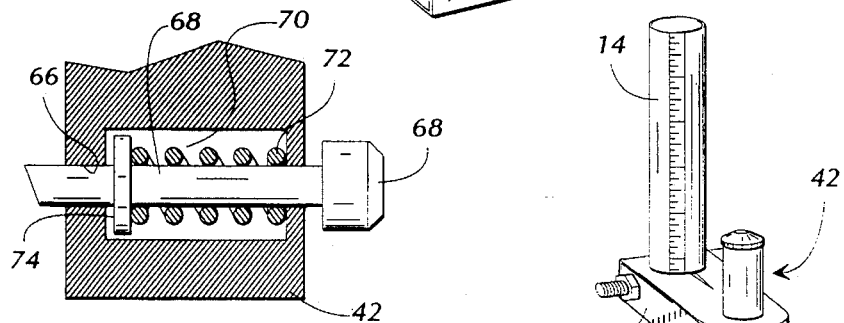
FIG. 7 is an enlarged view of a portion of the latch-release device.

As seen in FIG. 4, the piston 50 is in the extended position as it would be after a percussion blow has been struck. To recharge the percussion assembly the operator pushes dome 54 against the bias of spring 60 until the latch member engages the lower surface of the ledge 76 formed intermediate the length of the piston 52. As can be readily understood, the percussion hammer, after charging against the spring 60, is activated by merely pulling latch 68 outwardly against the bias spring 72. An enlarged cross section of the activating latch pin 68 is shown in FIG. 7. The coil spring 72 urges the pin inwardly against the spring 72 but the spring is sufficiently elastic so that an operator can readily pull the latch outwardly so that the dome 54 will strike home against its desired target.

Figure 5:
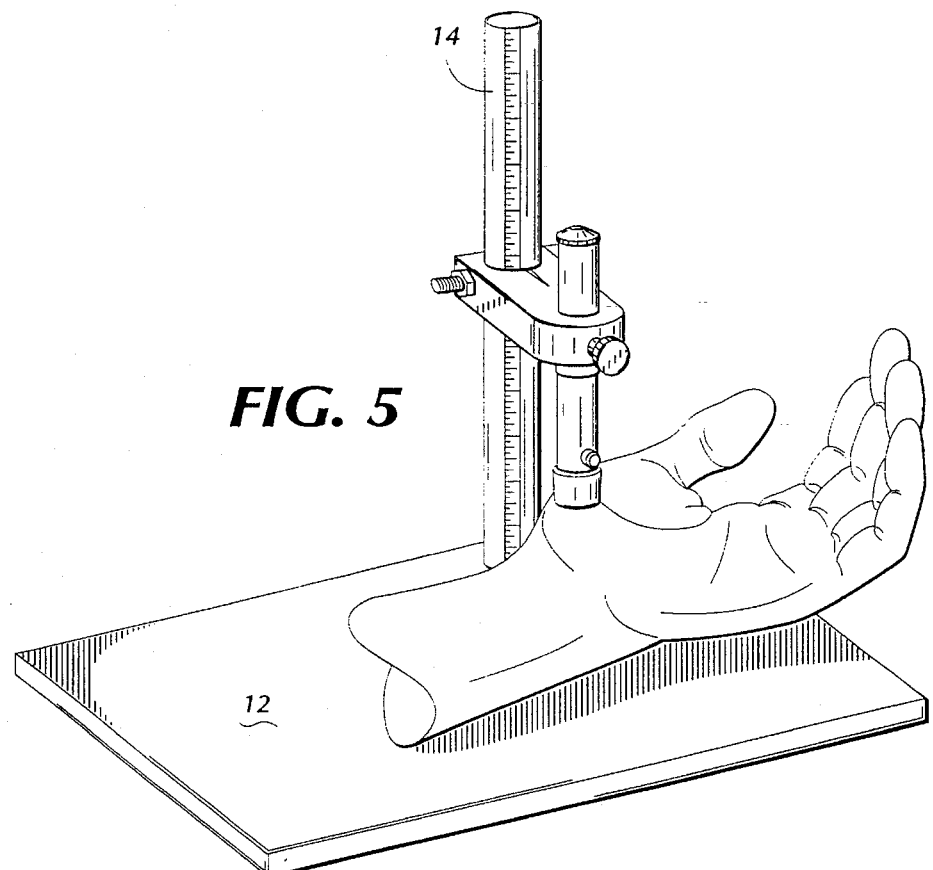
FIG. 5 is a perspective view of a patient's arm located below and at a proper distance from the percussion hammer.
Figure 6:
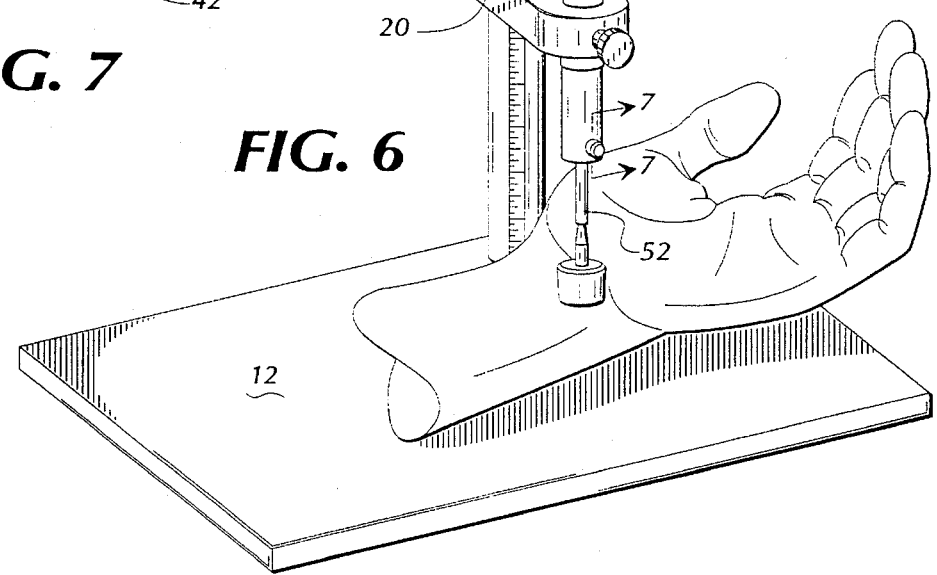
FIG. 6 is a view similar to FIG. 5 with the percussion hammer extended and having struck the desired area.

The operation of the device can be best understood by reference to FIGS. 5 and 6. As previously mentioned, many tests are conducted to determine what degree of impact will cause a tingling in a normal person's nerve and then arrive at an incremental amount just below that impact to test for the healing progress in a damaged nerve. In testing, the technician will place an arm with a normal nerve network, as seen in FIG. 5, and subject a particular nerve by impacting it with dome 54. Springs of different magnitudes are used to apply different forces.

The bracket 20 is placed along the length of standard 14 at a selected point so that there will be uniformity of impact. For instance, it is often advisable to place the bracket 20 so that the surface of the body (the wrist here) is in the area of the last 10%–20% of the piston 58's stroke. It is important to note that the distance be kept constant during a particular test run. It has been found that good readings can be obtained during the last 10%– 20% of the piston's stroke. The important factor is that if a 20% figure is selected, all of the testing must be done at 20% from the end of the stroke. By using this procedure graphs and test results are compiled to advise the treating physician of the force level and distance which will provide accurate results.

A test group of subjects known to have healthy nerve networks are tested. Each subject has his or her nerves struck by the hammer at progressively greater force levels. The point or force level where Tinel's sign is sensed, is noted.

The average of these forces is computed. A force just under said average force level is selected for patient purposes.

In treatment, the physician will place the arm of a patient in the same position as that shown in FIGS. 5 and 6 and administer impacts in accordance with the just under force level given to him. The physician can be given eight or nine of the hammer's 42, each containing a spring of different force level. Another method is to provide the physician with one of the elements 42 but with plurality of force springs 60 having different force levels.

The unit measurements of the springs and impact members is immaterial. The springs used by the inventor are measured in pounds. The important feature for good results is that the striking force can be regularized to obtain good test results and then be able to drop the striking force below that of the test results.

For example, presume that the testing of the healthy nerve network group discloses that a particular healthy nerve will tingle if struck by the dome with 3.2 pound spring. Then, the physician will mount the bracket at the same distance and strike the nerve with 3.0 pound spring. If tingling occurs, he is quite certain that this was not a false Tinel signal.

While changes may be made in the details of construction and some variance can be made in the methods described, it is to be understood that such changes are deemed to be within the spirit and scope of the invention as defined by the patented claims.

I claim:

1. A method of determining the presence of a Tinel's sign in a nerve patient comprising the steps of:
   selecting a group of test subjects known to have healthy nerve networks;
   striking selected nerves of each of said subjects with a hammer at progressively greater force levels until said subject senses a Tinel's sign at that force level;
   noting said force level at which Tinel's sign is sensed by a subject;
   averaging said force level of said group of test subjects to arrive at a selected average force; and
   subjecting the nerve of a nerve patient to a test force just under said selected average force so that if said patient detects Tinel's sign at said test force, a relatively accurate determination of regeneration can be recorded.

2. The method of claim 1 wherein said method includes the further step of accurately locating the nerve of said patient under a striking implement and locating said nerve at a selected distance along the path of said striking implement.

3. The method of claim 1 wherein a striking implement is movably mounted on a vertical standard and said locating steps are accomplished by placing said selected nerve below said implement and is secured at a selected distance from said nerve.

4. The method of claim 3 wherein said method includes the further step of providing a base for the reception of a body part containing said nerve.

5. A nerve testing system comprising a series of devices for individually striking the exterior of a person's body near a particular nerve wherein each of said devices includes a cylinder movably mounted on a standard, a piston reciprocally received in said cylinder and having a retracted position and an extended position, a spring biasing said piston to said extended position, a lock means for holding said piston in said retracted position and operator control means for permitting said piston to move from said retracted position to said extended position, wherein the improvement comprises:
   a base member upon which a limb of a patient can rest;
   said standard extending vertically upward from said base;
   means adjustably mounting said cylinder on said standard so that the distance between said limb and said extended position can be selected;
   a removable cap for enclosing each of said cylinders; and
   coil springs having varying strengths adapted to be individually received in said cylinder and secured in place by said cap so that an operator can administer impacts of varying degrees by selecting a particular one of said springs.

\* \* \* \* \*